(12) United States Patent
Sandstrom

(10) Patent No.: US 9,050,474 B2
(45) Date of Patent: Jun. 9, 2015

(54) TRANSFER RESISTANT COSMETIC

(75) Inventor: Giovana A. Sandstrom, Saddle Brook, NJ (US)

(73) Assignee: Avon Products, Inc, New York, NY (US)

( * ) Notice: Subject to any disclaimer, the term of this patent is extended or adjusted under 35 U.S.C. 154(b) by 0 days.

(21) Appl. No.: 13/395,330

(22) PCT Filed: Oct. 4, 2010

(86) PCT No.: PCT/US2010/051259
§ 371 (c)(1),
(2), (4) Date: Mar. 9, 2012

(87) PCT Pub. No.: WO2011/059593
PCT Pub. Date: May 19, 2011

(65) Prior Publication Data

US 2012/0207801 A1   Aug. 16, 2012
US 2014/0004162 A9   Jan. 2, 2014

Related U.S. Application Data

(60) Provisional application No. 61/259,679, filed on Nov. 10, 2009.

(51) Int. Cl.

| | |
|---|---|
| A61Q 1/06 | (2006.01) |
| A61K 8/02 | (2006.01) |
| A61K 9/20 | (2006.01) |
| A61K 8/25 | (2006.01) |
| A61K 8/26 | (2006.01) |
| A61K 33/08 | (2006.01) |
| A61K 8/11 | (2006.01) |
| A61K 8/19 | (2006.01) |
| A61K 8/29 | (2006.01) |
| A61K 8/895 | (2006.01) |
| A61Q 1/02 | (2006.01) |

(52) U.S. Cl.
CPC ... *A61Q 1/06* (2013.01); *A61K 8/02* (2013.01); *A61K 9/2036* (2013.01); *A61K 8/25* (2013.01); *A61K 33/08* (2013.01); *A61K 8/11* (2013.01); *A61K 8/19* (2013.01); *A61K 8/26* (2013.01); *A61K 8/29* (2013.01); *A61K 8/895* (2013.01); *A61K 2800/412* (2013.01); *A61K 2800/57* (2013.01); *A61Q 1/02* (2013.01)

(58) Field of Classification Search
CPC ............ A61Q 1/02; A61Q 1/06; A61Q 1/10; A61Q 1/04; A61K 8/25; A61K 8/8152
See application file for complete search history.

(56) References Cited

U.S. PATENT DOCUMENTS

| | | | |
|---|---|---|---|
| 5,262,087 A * | 11/1993 | Tachibana et al. | 516/23 |
| 6,458,390 B1 | 10/2002 | Manelski et al. | |
| 2003/0031636 A1 | 2/2003 | Scancarella et al. | |
| 2003/0072728 A1 | 4/2003 | Soane et al. | |
| 2004/0096407 A1 | 5/2004 | Scancarella et al. | |
| 2004/0126346 A1 * | 7/2004 | Martin et al. | 424/64 |
| 2006/0088486 A1 | 4/2006 | McNamara et al. | |
| 2006/0134035 A1 | 6/2006 | Zheng et al. | |
| 2007/0020208 A1 * | 1/2007 | Gutkowski et al. | 424/63 |
| 2007/0093619 A1 * | 4/2007 | Bui et al. | 525/477 |
| 2007/0196291 A1 * | 8/2007 | Sakuta | 424/59 |
| 2007/0274941 A9 | 11/2007 | Blin | |
| 2011/0110992 A1 * | 5/2011 | Garrison et al. | 424/401 |

FOREIGN PATENT DOCUMENTS

| | | |
|---|---|---|
| EP | 1334712 A2 | 8/2003 |
| WO | 2009/082565 A1 | 2/2009 |
| WO | 2009/111128 A1 | 9/2009 |
| WO | WO 2009111128 A1 * | 9/2009 |

OTHER PUBLICATIONS

Product New [oneline]. Adina Cosmetic Ingredients, Nov. 2006, retrieved from the Internet: <URL:http://www.cosmetic ingredients.co.uk/adinaformulate06.pdf>.

* cited by examiner

*Primary Examiner* — Brian-Yong Kwon
*Assistant Examiner* — Mark V Stevens
(74) *Attorney, Agent, or Firm* — David M. Joyal; Joan M. McGillycuddy

(57) ABSTRACT

Provided are cosmetic compositions comprising acrylate film forming polymers and an surface-treated colorants which exhibit an improved or synergistic reduction in their propensity to transfer or rub of during wear.

16 Claims, 1 Drawing Sheet

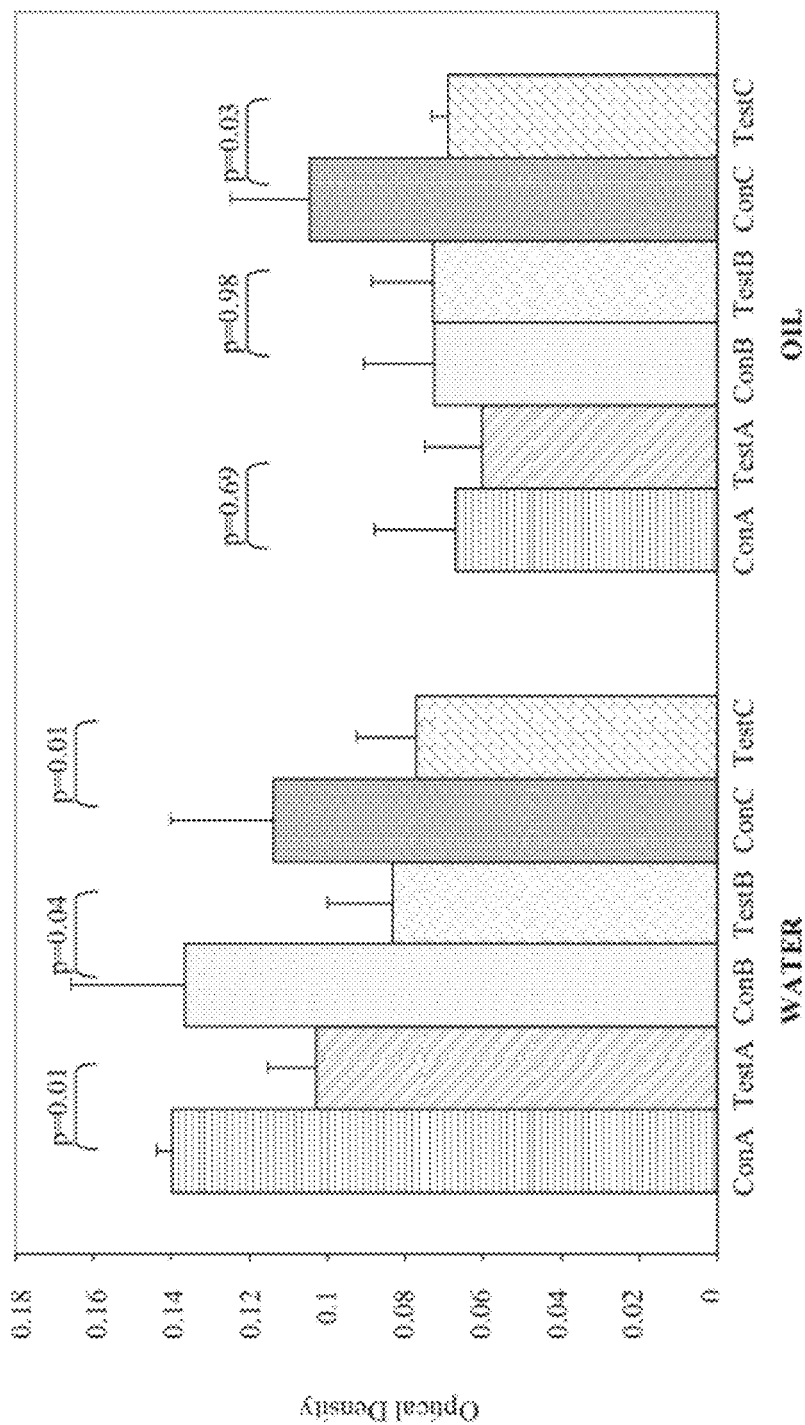

ID
TRANSFER RESISTANT COSMETIC

CROSS REFERENCE TO RELATED APPLICATIONS

This application claims priority to International Application Serial No. PCT/US10/51259 filed Oct. 4, 2010, the contents of which are hereby incorporated by reference in their entirety, and claims priority to U.S. Provisional Patent Application Ser. No. 61/259,679 filed Nov. 10, 2009.

FIELD OF INVENTION

The present invention relates generally to color cosmetics having a reduced propensity to transfer or rub-off during wear. More particularly, the invention relates to color cosmetics comprising film forming polymers derived from acrylic acid in combination with a colorant comprising an alumina, substrate having a colorant bonded thereto.

BACKGROUND

The ability of a cosmetic product to remain on a surface (e.g., skin, lips, hair, eyelashes, etc.) is commonly referred to as "transfer resistance." Ideally, a cosmetic film should lasts until the consumer wants to remove it by washing with water or using remover compositions. However, many cosmetics are deficient in this regard and readily transfer to the fingers, napkins, clothing, utensils, cups, and the like. This problem is particularly disadvantageous with color cosmetics, such as lipsticks, foundations, and mascara, where clothing can become discolored on contact and the cosmetic must be frequently re-applied to maintain a fresh appearance. Thus, much effort has been directed to developing so-called transfer-resistant cosmetics.

Transfer-resistant cosmetics typically employ a film forming polymer to provide a long-wearing film of the skin, lips, hair or lashes and to aid in spreading and adhering the formulation to the surface. The class of polymers known as organosiloxanes, including polydimethylsiloxane (PDMS or Dimethicone), have received considerable attention as film-formers in cosmetic products due to their excellent spreading properties and biological inertness. More recently, the properties of silicone polymers have been modified by copolymerization with other polymers, such as polyurethanes, ethylenically unsaturated monomers or polymers thereof, and the like.

For example, in U.S. Patent Pub. 2008/0019932, the disclosure of which is hereby incorporated by reference. Revlon describes color cosmetic compositions comprising "at least one silicone film forming polymer, at least one pigment, and at least one dispersant that aids in dispersion of the pigment and silicone film forming polymer in the composition." The silicone film forming polymer may be, among others, a silicone acrylate. However, Revlon makes no mention of the transfer-resistance or long-wear benefits associated with silicone acrylate film formers in color cosmetics.

There is a need for color cosmetics which exhibit a diminished propensity to transfer or rub-off once applied to the skin, lips, or hair or a user and which exhibit longer-wear than the presently available products. It is therefore an object of the invention to provide transfer-resistant cosmetics, and in particular, transfer resistant cosmetics comprising silicone acrylate polymers, preferably in synergistic combinations with certain colorants.

SUMMARY OF THE INVENTION

In accordance with the foregoing objectives and others, it has surprisingly been found that forming polymers derived from acrylic acid and a colorant comprising an alumina substrate having a pigment or lake bonded thereto cooperate synergistically to enhance the transfer resistance of color cosmetics. In other words, the inventive cosmetic compositions exhibit unexpectedly enhanced transfer resistance in comparison with otherwise identical compositions containing other film formers or other particulate colorants. The film forming polymer derived from acrylic acid may include, for example, acrylic acid monomers, esters of acrylic acid monomers (acrylates), alkyl-substituted acrylic acid and/or acrylates, and the like, as well as block or graft copolymers comprising such film forming polymer derived from acrylic acid. For example, a silicone acrylate film former, in particular a film forming polymer comprising a dimethicone polymer grafted onto a side chain of a (alkyl)acrylate copolymer, is preferred. The particulate colorant comprises an alumina substrate, which may be in any form, including without limitation, a platelet or sphere, and has an inorganic pigment or lake bonded to the surface of the alumina substrate. In some embodiments, the colorant may be hydrophobically modified by surface treatment to improve dispersibility in the film former. The surface treatment will preferably attach alkylsilane (e.g, octylsilane) groups on the surface of the colorant by, for example, treatment with triethoxy alkylsilane or the like. The cosmetic compositions are suitably formulated as a lipstick, a lip gloss, mascara, concealer, nail enamel, foundation, or similar cosmetics for which transfer resistance is desired. A synergistic reduction in either or both of water-transfer or oil-transfer resistance is contemplated.

These and other aspect of the invention will be better understood by reference to the following detailed description, including the Figures and appended claims.

BRIEF DESCRIPTION OF THE DRAWINGS

FIG. 1 shows the average transfer (optical density; y-axis) ±SEM of film drawn from control lipsticks (ConA, ConB, ConC; x-axis) or test lipsticks (TestA, TestB, TestC, x-axis) to Styrofoam discs in the presence of water or oil, n=5 for each.

DETAILED DESCRIPTION

The compositions of the invention comprises a film forming polymer derived from acrylic acid and a colorant comprising an alumina substrate having a pigment or lake bonded thereto. By derived from acrylic acid is meant that the polymers are the reaction products of monomers which include α-unsaturated carboxylic acid or carboxylate groups, for example, acrylic acid monomers, esters of acrylic acid monomers (acrylates), alkyl-substituted acrylic acid and/or acrylates, and the like, as well as block or graft copolymers comprising such film forming polymer derived from acrylic acid. The term (alkyl)acrylate is meant to include polymers and copolymers of acrylic acid monomers or esters of acrylic acid monomers.

The composition may further include any ingredients suitable or customary for inclusion in the particular type of cosmetic. The film forming polymer and colorant are preferably present in synergistic amounts, by which is meant relative ratios on a weight basis which impart unexpected reductions in the transfer of colorant from a cosmetic film.

I. Film Forming Polymer

The film forming polymers of the invention will typically be the reaction products of ethylenically unsaturated monomers having carboxylic acid or esters functional groups. Such monomers may have the following structure:

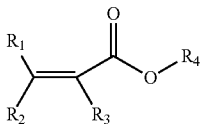

where $R_1$, $R_2$, and $R_3$ are independently selected from hydrogen or a $C_1$-$C_{10}$ hydrocarbon radical, including, for example, methyl, ethyl, propyl, iso-propyl, n-butyl, iso-butyl, tert-butyl, pentyl (amyl), hexyl, cyclohexyl, heptyl, octyl, phenyl, benzyl, and the like. In some monomers $R_1$, $R_2$ and $R_3$ will be hydrogen. Such monomers are known generally as acrylic acid or acrylate monomers. In other monomers $R_1$ and $R_2$ will be hydrogen and $R_3$ will be methyl. Such monomers will be recognized as methacrylic acid or methacrylate monomers. The term (meth)acrylic or (meth)acrylate refers to the situation where $R_3$ can be either hydrogen or methyl. The term (alkyl)acrylic or (alkyl)acrylate refers to the situation where $R_3$ can be either hydrogen or alkyl. That is, the parenthetical, in each case, indicates that the alkyl substitution is optional.

$R_4$ is independently selected from hydrogen or a $C_1$-$C_{10}$ hydrocarbon radical, including, for example, methyl, ethyl, propyl, iso-propyl, n-butyl, iso-butyl, tert-butyl, pentyl (amyl), hexyl, cyclohexyl, heptyl, octyl, phenyl, benzyl, and the like. Any of the foregoing groups can be straight chained or branched and may optionally include one or more points of unsaturation. These hydrocarbon radicals may also optionally be substituted with one or more heteroatoms, including halogen (F, Cl, Br, I), oxygen, nitrogen, sulfur, and the like. Perhalo-derivatives are also contemplated, including per-fluoro-derivatives such as trifluoromethyl.

The film forming polymers of the invention may be graft copolymers and may include one or more monomers having organosilicone polymers grafted onto a hydrocarbon group. $R_4$ may be, for example, a moiety of the form:

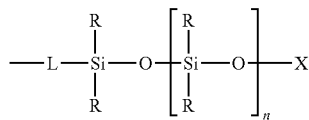

where L is a linker comprised of a di-valent $C_1$-$C_{20}$ hydrocarbon radical, such as methylene (—$CH_2$—), ethylene (—$CH_2CH_2$—), propylene (—$CH_2CH_2CH_2$—), butylene (—$CH_2CH_2CH_2CH_2$—), or the like; R is independently selected from hydrogen or a $C_1$-$C_{10}$ hydrocarbon radical, including, for example, methyl, ethyl, propyl, iso-propyl, n-butyl, iso-butyl, tert-butyl, pentyl (amyl), hexyl, cyclohexyl, heptyl, octyl, phenyl, benzyl, and the like; and X is a capping group which may be, for example, any of the foregoing hydrocarbon radicals, or may be a group —$Si(R)_3$ where R is independently selected at each occurrence and is preferably methyl at each occurrence; and n is an integer from 1 to 200, typically from 5 to 100, or from 10 to 50.

In some embodiments, R is selected independently at each occurrence from hydrogen, hydroxyl, and optionally substituted hydrocarbon groups containing from 1 to 10 carbon atoms, and in particular from optionally substituted alkyl, alkenyl, alkynyl, aryl, alkyl-aryl, or aryl-alkyl groups; preferably R is selected from optionally substituted branched, straight chain, or cyclic $C_{1-6}$ alkyl or alkenyl groups, including without limitation, methyl, ethyl, propyl, isopropyl, butyl, isobutyl, t-butyl, amyl, hexyl, cyclohexyl, vinyl, allyl, and the like or $C_{1-8}$ aryl, alkyl-aryl, or aryl-alkyl groups, including without limitation, phenyl, benzyl, tolyl, xylyl and the like;

wherein each of the foregoing R groups may include optional substitution by one or more heteroatoms, including oxygen, nitrogen, phosphorous, and halogen, particularly fluorine, as exemplified by fluoroalkyl (including perfluoro-alkyl) groups, such as mono-, di-, and trifluoromethyl, per-fluorophenyl, and the like, amino-substituted $C_{1-6}$ alkyl groups, including those having the form —$(CH_2)_{1-6}$—$NR^N_2$ and —$(CH_2)_{1-6}$—$NR^N$—$(CH_2)_{1-6}$—$NR^N_2$ where $R^N$ is typically hydrogen, but may be methyl, ethyl, propyl, and the like; polyether groups including without polyethyleneoxide groups of the form —$(CH_2CH_2O)_n$—, polypropylene oxide groups of the form —$(CH(CH_3)CH_2O)_n$— and combinations thereof; and amine oxide, phosphate, hydroxyl, ester, and/or carboxylate functionalities, and the like;

In a preferred embodiment $R_4$ comprises a dimethicone polymer of the form:

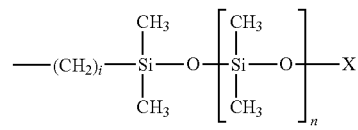

where i is an integer from 1 to 20, typically from 1 to 10, and preferably is 2, 3, 4, 5, or 6; and X is a chain terminating group, which may be, for example, hydrogen, alkyl, or —$Si(R)_3$ where R is independently selected at each occurrence from the R groups listed above, but is preferably methyl at each occurrence; and n is an integer from 1 to 200, typically from 5 to 100, and preferably from 10 to 50, and more preferably from 15 to 35.

Any of the foregoing hydrocarbon groups can be straight-chained or branched and may optionally include one or more points of unsaturation. The hydrocarbon radicals may also optionally be substituted with one or more heteroatoms, including halogen (F, Cl, Br, oxygen, nitrogen, sulfur, and the like. Perhalo-derivatives are also contemplated, including perfluoro-derivatives such as trifluoromethyl. The silicone polymer portion of $R_4$ may comprise, for example, methicone, dimethicone, amodimethicone, $C_1$-$C_6$ organosilicone, $C_1$-$C_6$ diorganosilicone, hydroxyalkylsilicone (e.g., hydroxypropyldimthicone), alkyl-arylsilicone, or like polymeric regions.

The polymers of the invention may be the reaction products of one, two, three, four, or more different ethylenically unsaturated monomers. In one embodiment the polymer is the reaction product of at least one acrylate monomer, at least one methacrylate monomer, and at least one (meth)acrylate monomer having a grafted silicone polymer in $R_4$.

The ethylenically unsaturated monomers having carboxylic acid or esters functional groups will typically comprise greater than about 50%, more typically greater than about 75%, preferably greater than about 85%, more preferably greater than about 90%, and more preferred still greater than about 95% of the monomers from which the film forming polymer is formed. In other embodiments, the film forming polymer will consist of or consist essentially of the reaction product of ethylenically unsaturated monomers having carboxylic acid or esters functional groups. By "consist essentially of" the reaction product of ethylenically unsaturated monomers having carboxylic acid or esters functional groups is meant that the polymer will not contain, or will contain such low levels of other monomers (excluding end or capping groups), such as ethylenically unsaturated monomers which do not comprise carboxylic acid or esters functional groups, that the properties of the polymer (e.g., transfer resistance) are not measurable impacted.

The compositions comprise one or more film formers derived from acrylic acid, and may suitably include, for example, two or three chemically distinct film formers derived from acrylic acid.

Specific mention may be made of silicone acrylate copolymers, including without limitation, those having the INCI names Butyl Acrylate/Hydroxypropyl Dimethicone Acrylate Copolymer (CTFA Monograph ID 12998), Acrylates/Dimethicone Copolymer (CTFA Monograph ID 10082), Acrylates/Ethylhexyl Acrylate/Dimethicone Methacrylate Copolymer (CTFA Monograph ID 16592), a combinations thereof, etc. In a preferred embodiment, the acrylate film former selected from the group consisting of Butyl Acrylate/Hydroxypropyl Dimethicone Acrylate Copolymer (CTFA Monograph ID 12998), Acrylates/Dimethicone Copolymer (CTFA Monograph ID 10082), and combinations thereof. Silicone acrylate polymers may suitably be solvated in an appropriated solvent, such as methyl trimethicone, isododecane (IDD), dimethylsiloxane, cyclodimethicone pentamer/hexamer, or the like. Is is contemplated that the use of silicone acrylate copolymers may impart both water and oil transfer resistance. Other suitable film formers may not comprise silicone polymers. Non-limiting examples of specific film formers derived from acrylic acid that are not silicone copolymers include, without limitation, Acrylates Copolymer (CTFA Monograph ID 52).

Generally, the film former is present in an amount from about 0.1 wt % to about 85 wt % by total weight of the composition. Typically, the film former is present from about 1% to about 75% by weight, more typically between about 5% and about 50%, and preferably, between about 10% and about 45% by weight, based on the total weight of the composition. These ranges also apply to combination of two or more different film formers.

II. Particulate Colorant Component

The second component of the invention is a particulate colorant which comprises (i) a particulate modifying agent; and (i) a first colorant bonded to the surface of the particulate modifying agent. As used herein, the term "colorant" generally refers to a color extender, dye, pigment, lake, toner, other agent, or a combination thereof, used to impart a color to a material, and includes inorganic, organic, water-soluble and water-insoluble substances. As used herein, the term "modifying agent" includes a substrate responsible for imparting additional optical or visual properties to the material.

The particulate colorant may be formed according to the procedures described in Sensient Colors Inc.'s U.S. Patent Pub. 2007/0020208, the disclosure of which is hereby incorporated by reference herein. For example, the particulate colorant may be prepared by blending, either in dry form or as slurries or solutions, the first colorant with the particulate modifying agent. The first colorant may be bonded to the surface of the particulate modifying agent by, for example, adding a surface treatment to the dry blend. By "bonded" is meant chemical bonding through strong interactions, for example, ionic or covalent bonds, or by physical bonding through weak interactions, for example, by dipole-dipole interactions such as hydrogen bonds, charge-transfer complexes, hydrophobic interactions, van der Waals forces, or combinations thereof.

The modifying agent may be, without limitation, a metal oxide, such as aluminum oxide (alumina), zinc oxide, silicon dioxide (silica), magnesia, or a combination thereof, talc; mica; kaolin; bismuth oxychloride; stainless steel; graphite; or platy metals such as bronze, copper and aluminum or a combination thereof. A preferred modifying agent comprises a metal oxide; in particular alumina. The modifying agent may be in the shape of a platelet, for example, a platelet of alumina. As used herein, the term "platelet" generally refers to a substantially planar and flaky material that is generally not spherical and is greater in width and length than in thickness. For example, suitable platelets may have an average diameter of between 1 and 20 microns, and an average thickness less than 0.5 microns. In some embodiments, the edge of the platelet is substantially free of colorant, by which is meant that at least 90% of the total surface area of the edge of the modifying agent has no colorant adhered or bonded to it. The top and bottom faces of the platelet will typically have the first colorant adhered to about 5% to about 90% of their surface area. In some embodiments, the first colorant may cover or coat more than about 1%, 3%, 5%, 10%, 15%, 20%, 30%, 40% or 50% of the total surface area of the modifying agent and less than about 99%, 95%, 90%, 85%, 80%, 75%, 65%, 50%, 40%, 30%, 25%, 20%, 15% or 10%, of the total surface area of the modifying agent. According to Sensient Colors Inc.'s U.S. Patent Pub. 2007/0020208, these particulate colorants may exhibit increased burnishing when compared with platelet alumina completely coated with colorant.

The first colorant may comprise, for example, an inorganic pigment. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Non-metal oxides such as alumina and silica, ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and the like, are also contemplated to be suitable inorganic pigments.

The first colorant may comprise, for example, an organic pigment. Organic pigments can include, but are not limited to, at least one of carbon black, carmine, phthalocyanine blue and green pigment, diarylide yellow and orange pigments, and azo-type red and yellow pigments such as toluidine red, litho red, naphthol red and brown pigments, and combinations thereof.

The first colorant component may comprise, for example, one or more dyes, toners or lakes. Lakes generally refer to a colorant prepared from a water-soluble organic dye (e.g., D&C or FD&C) which has been precipitated onto an insoluble reactive or adsorptive substratum or diluent. The term "D&C" means drug and cosmetic colorants that are approved for use in drugs and cosmetics by the FDA. The term "FD&C" means food, drug, and cosmetic colorants which are approved for use in foods, drugs, and cosmetics by the FDA. Certified D&C and FD&C colorants are listed in 21 C.F.R. §74.101 et seq. and include the FD&C colors Blue 1, Blue 2, Green 3, Orange B, Citrus Red 2, Red 3, Red 4, Red 40, Yellow 5, Yellow 6, Blue 1, Blue 2; Orange B, Citrus Red 2; and the D&C colors Blue 4, Blue 9, Green 5, Green 6, Green 8, Orange 4, Orange 5, Orange 10, Orange 11, Red 6, Red 7, Red 17, Red 21, Red 22, Red 27, Red 28, Red 30, Red 31, Red 33, Red 34, Red 36, Red 39, Violet 2, Yellow 7, Yellow 8, Yellow 10, Yellow 11, Blue 4, Blue 6, Green 5, Green 6, Green 8, Orange 4, Orange 5, Orange 10, Orange 11, and so on.

Substrates suitable for forming lakes include, without limitation, mica, bismuth oxychloride, sericite, alumina, aluminum, copper, bronze, silver, calcium, zirconium, barium, and strontium, titanated mica, fumed silica, spherical silica, polymethylinethacrylate (PMMA), micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, nylon, silica silylate, silk powder, sericite, soy flour, tin oxide, titanium hydroxide, trimagnesium phosphate, walnut shell powder, and mixtures thereof.

Suitable lakes include, without limitation, those of red dyes from the monoazo, disazo, fluoran, xanthene, or indigoid families, such as Red 4, 6, 7, 17, 21, 22, 27, 28, 30, 31, 33, 34, 36, and Red 40; lakes of yellow pyrazole, monoazo, fluoran, xanthene, quinoline, dyes or salt thereof such as Yellow 5, 6, 7, 8, 10, and 11; lakes of violet dyes including those from the anthroquinone family, such as Violet 2, as well as lakes of orange dyes, including Orange 4, 5, 10, 11, and the like. Suitable Lakes of D&C and FD&C dyes are defined in 21 C.F.R. §82.51.

The surface treatment may be any such treatment that modifies the surface of the modifying agent. For example, the surface treatment may make the particles more hydrophobic or more dispersible in a vehicle or may increase the adhesion of the first colorant to the modifying agent. The surface of the particles may, for example, be covalently or ionically bound to an organic molecule or silicon-based molecule or may be adsorbed thereto, or the particle may be physically coated with a layer of material. The surface treatment compound may be attached to the particle through any suitable coupling agent, linker group, or functional group (e.g., silane, ester, ether, etc). The compound may comprise a hydrophobic portion which may be selected from, for example, alkyl, aryl, allyl, vinyl, alkyl-aryl, aryl-alkyl, organosilicone, diorganosilicone, dimethicones, methicones, polyurethanes, silicone-polyurethanes, and fluoro- or perfluoro-derivatives thereof. Other hydrophobic modifiers include lauroyl lysine, Isopropyl Titanium Triisostearate (ITT), ITT and Dimethicone (ITT/Dimethicone) cross-polymers, ITT and Amino Acid, ITT/Triethoxycaprylylsilane Crosspolymer, waxes (e.g., carnauba), fatty acids (e.g., stearates), HDI/trimethylol Hexylactone Crosspolymer, PEG-8 Methyl Ether Triethoxysilane, aloe, jojoba ester, lecithin, Perfluoroalcohol Phosphate, and Magnesium Myristate (MM), to name a few.

The surface treatment may comprise, in some embodiment, a material selected from aluminum laurate, aluminum stearate, an amino acid, chitin, collagen, fluorochemical, lecithin metal soap, natural wax, polyacrylate, polyethylene, silicone, silane, titanatate ester, urethane, dimethicone, perfluoropolymethylisopropyl ether, styrene acrylates copolymer, magnesium myristate, lauroyl lysine and a combination thereof. In other embodiments, the surface treatment comprises a material selected from methicone, triethoxycaprylyisilane, trimethoxycaprylylsilane, dimethicone copolyol and a combination thereof.

In one embodiment, the particulate colorant has been surface treated with an alkylsilane, such as a $C_{1-20}$ alkylsilane, or more typically a $C_{1-12}$ alkylsilane, including an exemplary embodiment wherein the particle is surface-treated with a $C_8$ alkylsilane (e.g., caprylylsilane). The colorants may be prepared, for example, by treating a particulate with a trialkoxy-alkylsdane, such as Triethoxycaprylyisilane (INCI).

In another embodiment, the particulate has been surface treated with a fluoroalkylsilane, and in particular a perfluoroalkylsilane, such as a $C_{1-20}$ perfluoroalkylsilane, or more typically a $C_{1-12}$ perfluoroalkylsilane, including an exemplary embodiment wherein the particulate colorant is surface-treated with a $C_8$ perfluoroalkylsilane. These may be prepared by treating a particulate colorant with a trialkoxyfluoroalkyl-silane, such as Perfluorooctyl Triethoxysilane (INCI). An example of such a compound is tridecafluorooctyltriethoxy silane, available from Sivento, Piscataway, N.J., under the trade name DYNASILANE™ F 8261.

In some embodiments, the alkyl silane surface-treated colorant consists essentially of or comprises an alumina substrate (e.g., platelet shaped) and a pigment, dye, or lake bonded to the alumina substrate by an alkyl silane surface treatment. Typically, the alkyl silane will be octylsilane and may be formed by treatment with Triethoxy Caprylylsilane. Nonlimiting examples of such colorants include, but are not limited to, Alumina/Titanium Dioxide/Triethoxycaprylylsilane 1% (COVALUMINE™ Atlas White AS), Alumina/D&C Red Aluminum Lake CTD/Triethoxycaprylylsilane 1% (COVALUMINE™ Red Rose AS), Alumina/D&C Red Aluminum Lake CTD/Triethoxycaprylylsilane 1% (COVALUMINE™ Sonoma Red AS), Alumina/Black Iron Oxide CTD/Triethoxycaprylyisilane 1% (COVALUMINE™ Sonoma Black AS), Alumina/D&C Red #6 Aluminum Lake CTD/Triethoxycaprylyisilane 1% (COVALUMINE™ Fire Red AS), Alumina/Yellow Iron Oxide CTD/Triethoxycaprylyisi-lane 1% (COVALUMINE™ Sonoma Yellow AS), Alumina/D&C Blue #1 Aluminum Lake CTD/Triethoxycaprylyisilane 1% (COVALUMINE™ Astral Blue AS), Alumina/Carmine CTD/Triethoxycaprylyisilane 1% (COVALUMINE™ Campari AS), Alumina/Yellow #5 CTD/Triethoxycaprylyisilane 1% (COVALUMINE™ Sunburst AS), Alumina/Triethoxycaprylyisilane 1%, and combinations thereof, each of which is available from SENSIENT™ Cosmetic Technologies LCW.

In one embodiment, a cosmetic composition as described herein comprises a total of about 0.1% to about 75% by weight of the particulate colorant component, based on the total weight of the composition. Typically, the s particulate colorant component will comprise from about 0.5% to about 50% by weight, more typically from about 1% to about 40% by weight, and preferably from about 2% to about 30% by weight of the total composition. In other embodiments the particulate colorant component will comprise from about 3% to about 25% by weight, more typically from about 4% to about 15% by weight, and preferably from about 5% to about 10% by weight of the total composition.

IV. Other Ingredients

1. Shine Agents

The cosmetic compositions of the invention may optionally include one or more agents that provide or enhance shine. Shine enhancing agents will typically have a refractive index greater than about 1.4, preferably greater than about 1.5 when measured as a film at 25° C. Suitable shine enhancing agents include without limitation, polyols, fatty esters, silicone oils, phenylpropyldimethylsiloxysilicate, polybutene, polyisobutene, hydrogenated polyisobutene, hydrogenated polycyclopentadiene, propyl phenyl silsesquioxane resins; lauryl methicone copolyol, perfluorononyl dimethicone, dimethicone/trisiloxane, methyl trimethicone, and combinations thereof. In one embodiment, the composition will comprise a shine-enhancing agent in an amount from about 0.1% to about 10% by weight, more preferably from about 1% to about 5% by weight, based on the total weight of the composition.

2. Waxes

The cosmetic compositions of present invention may optionally include one or more waxes. The one or more waxes can be natural (e.g., vegetable, animal, or mineral) waxes or synthetic waxes (e.g., polyolefine, Fisher Tropsch, etc.). A preferred wax is microcrystalline waxes, which will preferably be composed of $C_8$ to $C_{50}$ hydrocarbons and will have a melting point preferably greater than about 60° C. Other waxes that may be mentioned include, without glyceryl tribehenate, candelilla, carnauba, ozokerite, paraffin, polyethylene, beeswax, ceresin, hydrogenated castor oil, japan wax, and mixtures thereof, in one embodiment, the amount of wax is less than about 2 wt % of the total weight of the composition. In another embodiment, the amount of wax ranges from about 0.1% to less than about 2% by weight based on the total weight of the composition. However, more wax can be used if clarity is not a concern. For example, a lip stick may comprise wax from about 5% to about 25% by weight based on the weight of the composition.

3. Pigments and Fillers

The cosmetic compositions may optionally further comprises various other pigments, pearlescents, dyes, lakes, and fillers, as is customary in a given product. These include, without limitation, metal oxide pigment such as iron oxides and titanium dioxide, silica, alumina, nylon powder, Teflon powder, PMMA, silicone elastomers, and the like. For other pigments, lakes and dyes used in cosmetic industry, refer to the Cosmetic Ingredient Dictionary (INCI) and Handbook, 12$^{th}$ Edition (2008), published by the Cosmetic, Toiletry, and Fragrance Association (CTFA), the disclosure of which is hereby incorporated by reference. Such additional pigments, fillers and the like will typically comprise from about 0.1% to about 20% by weight of the composition, more typically from about 0.8% to about 10% by weight of the composition.

4. Film Formers

In addition to the film formers of the invention which act synergistically with the alumina-based pigments to prevent or inhibit transfer of the cosmetic, other water-soluble, water-dispersible, or water-insoluble film formers, including film forming polymers, may be employed. The term film-forming polymer may be understood to indicate a polymer which is capable, by itself or in the presence of at least one auxiliary film-forming agent, of forming a continuous film which adheres to a surface and functions as a binder for the particulate material.

Polymeric film formers include, without limitation, acrylic polymers or co-polymers, acrylates, polyolefins, polyvinyls, polacrylates, polyurethanes, silicones, polyamides, polyethers, polyesters, fluoropolymers, polyethers, polyacetates, polycarbonates, polyamides, polyimides, rubbers, epoxies, formaldehyde resins, organosiloxanes, dimethicones, methicones, cellulosics, polysaccharides, polyquaterniums, and the like. Suitable film formers include those listed in the Cosmetic Ingredient Dictionary (INCI and Handbook, 12$^{th}$ Edition (2008), the disclosure of which is hereby incorporated by reference.

5. Cosmetically Acceptable Vehicles

The compositions will typically comprise a cosmetically acceptable vehicle. By "cosmetically acceptable" is meant that the vehicle is safe for contact with human skin. It is contemplated that any cosmetically acceptable vehicle known in the art will be useful. The vehicle may comprise water, hydrophobic, and/or hydrophilic solvents.

Suitable hydrophilic solvents include but are not limited to, water, isopropyl alcohol, ethyl alcohol, glycerin, butylene glycol, propylene glycol, pentylene glycol, caprylyl glycol, polyglycerol diisostearate, dimethylsiloxane/glycol copolymer, isopropyl myristate, triisostearyl citrate, or any combinations thereof. Suitable hydrophobic vehicles include volatile or non-volatile hydrocarbon oils, silicones, fatty ester oils, and the like.

The compositions may comprise at least one high evaporation rate solvent in combination with at least one medium evaporation rate solvent and/or at least one slow evaporation rate solvent. As used herein, a high evaporation rate solvent may be characterized as a solvent that exhibits about 20% to about 40% weight loss at 35° C. over 60 minutes and/or about 40% to about 50% weight loss at 35° C. over 120 minutes. A medium evaporation rate solvent may be characterized as a solvent that exhibits about 10% to about 15% weight loss at 35° C. over 60 minutes and/or about 20% to about 30% weight loss at 35° C. over 120 minutes. A slow evaporation rate solvent may be characterized as a solvent that exhibits less than about 10% weight loss at 35° C. over 60 minutes and/or about 5% to about 15% weight loss at 35° C. over 120 minutes. Non-limiting example of high evaporation rate solvents include hexamethyl disiloxane and/or a silicone fluid having a viscosity of less than 1 cSt at 25° C., including, for example, those silicone fluids having a viscosity of 0.65 cSt. A non-limiting example of a medium evaporation rate solvent include mixed dimethicones, e.g., a dimethicone/trisiloxane blend. Non-limiting examples of slow evaporation rate solvents include cyclopentasiloxane, methyl trimethicone, and isododecane.

The compositions of the invention may, in some embodiments, be provided as anhydrous formulations. By "anhydrous" is mean that the weight percentage of water in the composition is less than about 1% by weight. Preferably, the anhydrous compositions are substantially free of water by which is meant that water is not deliberately added to the compositions and the level of water is no more than would be expected based on the absorption of water from the air.

The vehicle may comprise from about 5% to about 99% by weight of the composition, typically from about 30% and about 90% by weight, and more typically from about 50% and about 70% by weight of the composition.

5. Emulsions

The compositions according to the invention may be formulated as water-in-oil (W/O) emulsions, oil-in-water (O/W) emulsions, water-in-silicone, silicone-in-water emulsions, and the like. These emulsions comprise a continuous phase and a discontinuous phase. The continuous phase may be aqueous, oil-based, or silicone-based and the discontinuous phase may likewise be aqueous, oil-based, or silicone-based, depending on the nature of the continuous phase. Combined oil and silicone phases are also possible.

The oil phase may comprise any of the hydrophobic oils discussed herein, including, without limitation, vegetable oils; fatty acid esters; fatty alcohols; isoparaffins such as isododecane; silicone oils such as dimethicones, cyclic silicones, and polysiloxanes; hydrocarbon oils such as mineral oil, petrolatum, isoeicosane and polyisobutene; natural or synthetic waxes; and the like.

The emulsions will typically comprise an amount of emulsifier sufficient to stabilize the emulsion. The amount of emulsifier will typically be from about 0.001 wt % to about 20 wt %, but preferably will range from about 0.01 to about 10 wt %, and most preferably about 0.1 wt % to about 5 wt %, based upon the total weight of the composition.

6. Emollients

The cosmetic compositions may optionally comprise one or more emollients in an amount from about 0.1% up to about 20% by weight, based on the total weight of the composition. More typically, emollients will be present in an amount from about 2 wt % to about 15 wt %, preferably, about 5 wt %. Emollients useful in the present invention include any known to the art, including, but not limited to, oils and esters, such as lanolin and petrolatum. Other emollients include jojoba oil, lanolin oil, coconut oil, palm kernel glycerides, grape seed oil, evening primrose oil, sesame oil, castor oil, meadowfoam seed oil, emu oil, dimethicone copolyol meadowfoamate, wheat germ oil, macadamia nut oil, avocado oil, and mixtures thereof.

7. Thickeners

The composition may comprise a thickener, such as vegetable gums, carboxymethyl cellulose, silica, acrylic acid polymers, clays, such as hectorites, bentonites, hydrated magnesium and aluminium silicates, or calcium silicates, or the like. When present, thickeners will comprise from about 0.1% to about 15% by weight of the composition, more typically from about 1% to about 5% by weight of the composition.

8. Other Ingredients

The composition may comprise one or more preservatives such as methyl, ethyl, or propyl paraben, and so on, in amounts ranging from about 0.0001 wt %-5 wt % by weight of the total composition. The compositions may have other ingredients such as one or more anesthetics, anti-allergenics, antifungals, anti-inflammatories, antimicrobials, antiseptics, chelating agents, emollients, emulsifiers, fragrances, humectants, lubricants, masking agents, medicaments, moisturizers, pH adjusters, preservatives, protectants, soothing agents, stabilizers, sunscreens, surfactants, thickeners, viscosifiers, vitamins, or any combinations thereof.

In addition, a cosmetic composition according to the present invention may comprise other ingredients and additives known in the art, depending on the purpose for which the cosmetic is intended. For example, a composition described herein may optionally include one or more functional agents, fillers and fragrances.

The compositions according to the invention may be useful in a variety of cosmetic and personal care products, including without limitation, lipsticks, and lipcolors, lip gloss, mascaras, transfer-resistant foundations, eyeliner, eyeshadow, water-proof sunscreens and insect repellents, skin care products, hair care products, antiperspirants and deodorants, and other cosmetic products where transfer resistant films are desired.

In another embodiment, the invention is formulated in a conventional lipstick or lipcolor product and may include, without limitation, any of the components disclosed in U.S. Pat. No. 6,509,009, U.S. Pat. No. 6,428,797, U.S. Pat. No. 6,261,576, U.S. Pat. No. 5,747,017, U.S. Pat. No. 5,318,775, and U.S. Pat. No. 4,935,228, the disclosures of which are hereby incorporated by reference.

EXAMPLES

Acrylate film forming polymers and alkyl silane surface-treated colorants synergistically enhance transfer resistance.

The transfer properties of three test lip compositions comprising octylsilane surface treated alumina-based colorant with one or more acrylate film formers (Test A-C) were compared to three control lip compositions comprising other pigments with one or more acrylate film formers (Control A-C). Additionally, the transfer properties of three test lip compositions comprising octylsilane surface treated alumina-based colorant in the absence of an acrylate film former (Test D-F) were compared to three control lip compositions comprising other pigments in the absence of an acrylate film former (Control D-F).

An octylsilane surface treated colorant consisting essentially of or comprising substrate, pigment, and alkyl silane generally is composed of about 50 wt % to about 75 wt % substrate (e.g., alumina platelet), about 25 wt % to about 50 wt % pigment metal oxide, organic dye, etc.) and about 1% alkyl silane Triethoxy Caprylylsilane). Because the alkyl silane surface-treated colorants used in this Example comprise a substrate, the total amount of alkyl silane surface-treated colorant added in the test samples was adjusted such that the test compositions comprised amounts of pigment that were comparable to the amounts of pigment comprised in the control compositions.

The compositions of the three test lip compositions and the three control lip compositions comprising one or more acrylate film formers are described in Tables 1 and 2, respectively, wherein all amounts are provided as weight percentage based on the entire weight of the composition.

TABLE 1

Compositions of three test lipsticks

| Ingredient | Test A | Test B | Test C |
|---|---|---|---|
| Butyl Acrylate | 18 | 18 | 0 |
| Dimethicone/Trisiloxane Blend | 31 | 76 | 49 |
| Silicone Acrylate | 45 | 0 | 45 |
| Alumina/Titanium Dioxide AS | 2 | 2 | 2 |
| Alumina/D&C Red Aluminum Lake with AS | 4 | 4 | 4 |
| Titanium Dioxide AS | 0 | 0 | 0 |
| Red 7 | 0 | 0 | 0 |

TABLE 2

Compositions of three control lipsticks

| Ingredient | Control A | Control B | Control C |
|---|---|---|---|
| Butyl Acrylate | 18 | 18 | 0 |
| Dimethicone/Trisiloxane Blend | 35.2 | 80.2 | 53.2 |
| Silicone Acrylate | 45 | 0 | 45 |
| Alumina/Titanium Dioxide AS | 0 | 0 | 0 |
| Alumina/D&C Red Aluminum Lake with AS | 0 | 0 | 0 |
| Titanium Dioxide AS | 0.8 | 0.8 | 0.8 |
| Red 7 | 1 | 1 | 1 |

The Alumina/Titanium Dioxide AS pigment and the Alumina/D&C Red Aluminum Lake with AS pigment listed in Tables 1 and 2 are commercially available from Sensient as Covalumine White AS and Covalumine Rose Red AS, respectively. Red 7 (CTFA. Monograph ID 670) is available from Sensient as Unipure Red LC 3079. The Silicone Acrylate polymer is dispersed in 0.65 cts silicone fluid, however, the amount listed in Tables 1 and 2 are based on the amount of active polymer.

The compositions of the three test lip compositions and the three control lip compositions comprising no acrylate film former are described in Tables 3 and 4, respectively, wherein all amounts are provided as weight percentage based on the entire weight of the composition.

TABLE 3

Compositions of three test lipsticks

| Ingredient | Test D | Test E | Test F |
|---|---|---|---|
| Phenylpropyldimethylsiloxysilicate | 18 | 18 | 0 |
| Dimethicone/Trisiloxane Blend | 31 | 76 | 49 |
| Cyclopentasiloxane dimethicone/ vinyltrimethylsiloxysilicate crosspolymer | 45 | 0 | 45 |
| Alumina/Titanium Dioxide AS | 2 | 2 | 2 |
| Alumina/D&C Red Aluminum Lake with AS | 4 | 4 | 4 |
| Titanium Dioxide AS | 0 | 0 | 0 |
| Red 7 | 0 | 0 | 0 |

TABLE 4

Compositions of three control lipsticks

| Ingredient | Control D | Control E | Control F |
|---|---|---|---|
| Phenylpropyldimethylsiloxysilicate | 18 | 18 | 0 |
| Dimethicone/Trisiloxane Blend | 35.2 | 80.2 | 53.2 |
| Cyclopentasiloxane dimethicone/ vinyltrimethylsiloxysilicate crosspolymer | 45 | 0 | 45 |
| Alumina/Titanium Dioxide AS | 0 | 0 | 0 |
| Alumina/D&C Red Aluminum Lake with AS | 0 | 0 | 0 |
| Titanium Dioxide AS | 0.8 | 0.8 | 0.8 |
| Red 7 | 1 | 1 | 1 |

The phenylpropyldimethylsiloxysilicate as listed in Tables 3 and 4 is commercially available from GE Bayer Silicones as SILSHINE™ 151.

Furthermore, the transfer properties of a test foundation comprising alkyl same surface treated colorant in the absence of an acrylate film former was compared to a control foundation comprising other pigments. The compositions of the test foundation and the control foundation are described in Table 3.

TABLE 3

Composition of control and test foundations

| Ingredient | Control | Test |
|---|---|---|
| Water | 57.44 | 40.92 |
| Thickeners | 1 | 1 |
| Preservatives | 1.15 | 1.15 |
| Humectant | 6 | 6 |
| Oil Absorbant | 0.9 | 0.9 |
| Filler | 1.5 | 1.5 |
| Emulsifier | 7.25 | 7.25 |
| Emollient | 7.5 | 7.5 |
| Dimethicone | 7 | 7 |
| Fragrance | 0.01 | 0.01 |
| Titanium Dioxide-Purified-Usp | 8 | 0 |
| Iron Oxide-Yellow | 1.16 | 0 |
| Cosmetic Red Oxide | 0.31 | 0 |
| Iron Oxide-Black | 0.18 | 0 |
| Pearl(s) | 0.6 | 0.6 |
| Alumina/Titanium Dioxide AS | 0 | 20 |
| Alumina/Yellow Iron Oxide AS | 0 | 4.7 |
| Alumina/Red Oxide AS | 0 | 0.95 |
| Alumina/Black Iron Oxide AS | 0 | 0.52 |

The Alumina/Titanium Dioxide AS pigment (Covalumine White AS), Alumina/Yellow iron Oxide AS (Covalumine Sonoma Yellow AS), Alumina/Red Oxide AS (Covalumine Sonoma Red AS), and Alumina/Black Iron Oxide AS (Covalumine Sonoma Black AS) pigments listed in Table 3 are each available from Sensient.

The method described below was utilized to determine the water and oil transfer resistances and adhesion properties of a cosmetic film. The method predicts the ability of a cosmetic film to resist color transfer to objects contacting the skin. Such objects include clothing, handkerchiefs or tissues, napkins and implements such as cups, glasses and tableware, and oily fingers or objects such as oily foods.

Films formed from cosmetic compositions exhibit a degree of transfer resistance directly proportional to the hardness and solvent-resistance of the film. The hardness and solvent-resistance may be expressed as a function of the Hot and rub test as described below.

Equipment:
(1) Glass plates;
(2) Collagen sausage casing such as Nippi Casing F Grade;
(3) Constant humidity chamber adjusted to 95% relative humidity;
(4) Utility Knife;
(5) Ruler;
(6) Single-sided adhesive tape;
(7) Double-sided adhesive tape;
(8) 25 micron thickness slot draw-down bar;
(9) White Styrofoam dinner plate such as Amoco Selectables™ Plastic DIA Tableware;
(10) 1.5 inch diameter circular metal punch;
(11) 1 kilogram weight;
(12) Vegetable oil;
(13) Brush-tip cosmetic applicator; and
(14) Lint-Free Wiper, such as Kimwipes® EX-L.

Procedure:
(1) Prepare a 3×4 inch sheet of collagen sausage casing by hydrating it in a 90% relative humidity chamber for at least 24 hours;
(2) Remove the collagen sheet to ambient conditions and immediately wrap tightly around the glass plate. Attach the collagen sheet to the glass using adhesive tape. The collagen surface should be flat and free of wrinkles;
(3) Allow the collagen-wrapped slide to equilibrate at ambient conditions for about 24 hours;
(4) Apply thin (1 mm), uniform films of a sample cosmetic composition on the collagen;
(5) Allow the cosmetic samples on the collagen surface to rest at ambient conditions for about one hour;
(6) Using a pipette, drop three drops of vegetable oil onto samples located the right side of the collagen surface. Using another pipet, drop three drops of water onto the left side of the collagen surface. Samples on the right side are used to determine the oil transfer resistance while samples on the left side are used to determine the water transfer resistance of the sample cosmetic composition;
(7) Separately for the oil and water sections, distribute the oil or water evenly over the surface of each cosmetic film sample using cosmetic brush applicators, brushing lightly;
(8) Allow the solvent to remain on the film undisturbed for about 15 minutes;
(9) Using a lint-free wiper, carefully blot excess solvent from the surface of each cosmetic film sample. Apply as little pressure as possible during this step;
(10) Cut two disks from a clean, white Styrofoam dinner plate using a 1.5 inch diameter circular punch. The surface and edges of each disk should be smooth and even;
(11) Firmly attach with double-sided adhesive tape each disk from step (10) to the bottom surface of a 1 kg weight;

(12) Set the weight on top of the cosmetic samples applied to the collagen surface from step (5) above so that a first disk is in contact with the oil section of the film the right side of the collagen surface) and a second disk is in contact with the water section of the film (i.e., the left side of the collagen surface). It is important to position the weight gently so that excess force beyond 1 kg is not applied;
(13) Grasping the top of the 1 kg weight, carefully rotate each disk through 360 degrees while maintaining the 1 kg force on the film. Do not lift or press the weight into the film during the rotating motion to the weight. The entire 360 degree rotation is preferably completed within a time interval between 3 and 5 seconds;
(14) Lift the weight straight up off the film surface and carefully remove the disk from the weight avoiding damage to the disk;
(15) Color transfer on each disk is visually assessed by comparing disks.

As described above, 1 mL of a test or control product were drawn on a collagen film and allowed to dry for 1 hour. Approximately 3 drops of oil were applied to the left side of the dried film and approximately 3 drops of water were applied to the right side of the dried film. The drops were distributed evenly over the film and allowed to remain for 15 min. A 1.5 inch Styrofoam disc was attached to the bottom of a 1 kg weight and set on top of the distributed water or oil. The weight was rotated 360° and then lifted off the film surface. Pictures of each Styrofoam disc were taken and the amount of color transfer to the disc was measured and quantified visually or with Image Pro Software that measured optical density.

As can be seen in Table 4, visual comparison of the lipsticks and foundations described above revealed that control lipsticks comprising non-treated pigment (e.g., pure titanium dioxide) demonstrated high transfer (one to two stars) in the presence of either or both butyl acrylate and silicone acrylate. In contrast, test lipsticks comprising alkyl silane surface treated colorant (e.g., Alumina/Titanium Dioxide AS and/or Alumina/D&C Red Aluminum Lake with AS) with either or both butyl acrylate and silicone acrylate (Test A-C) showed enhanced transfer resistance (two to three stars) compared to respective control lipsticks (Control A-C).

Control lipsticks comprising an non-treated pigment (e.g., pure titanium dioxide) demonstrated high transfer (two to three stars) in the absence of an acrylate film former. In contrast to test lipstick comprising one or more acrylate film formers, test lipsticks comprising alkyl silane surface treated colorant in the absence of an acrylate film former (Test D-F) demonstrated similar or higher transfer (one to two stars) than respective control lipsticks (Control D-F).

Furthermore, the test foundation comprising alkyl silane surface treated colorant in the absence of an acrylate film former did not demonstrate enhanced transfer resistance compared to the control foundation.

TABLE 4

| Sample | Styrofoam | Collagen |
| --- | --- | --- |
| Water Transfer Resistance | | |
| Control A | * | ** |
| Test A | ** | ** |
| Control B | * | * |
| Test B | ** | * |
| Control C | * | ** |
| Test C | ** | *** |
| Control D | ** | *** |
| Test D | * | ** |
| Control D | ** | ** |
| Test E | * | ** |
| Control E | ** | ** |
| Test E | ** | ** |
| Control foundation | * | ** |
| Test foundation | * | ** |
| Oil Transfer Resistance | | |
| Control A | ** | * |
| Test A | *** | * |
| Control B | ** | * |
| Test B | ** | * |
| Control C | * | * |
| Test C | ** | * |
| Control 1 | ** | ** |
| Testing 1 | * | * |
| Control 2 | ** | * |
| Testing 2 | ** | * |
| Control 3 | ** | * |
| Testing 3 | * | * |
| Control foundation | *** | ** |
| Test foundation | *** | *** |

Shown in FIG. 1 are the optical densities of Styrofoam discs lifted off water or oil dispersed on film formed by the control or test lipsticks described above. Test A, B, and C lipsticks had significantly less transfer in water compared to control A, B, and C lipsticks, respectively (FIG. 1). Only test lipstick C had significantly less transfer in oil compared to control C lipstick (FIG. 1). Taken together, these data indicate that an acrylate film former and an alkyl silane surface-treated alumina-based colorant synergistically enhance the transfer resistance of a cosmetic composition.

All patents and patent publications referred to herein are hereby incorporated by reference. Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. A transfer-resistant cosmetic composition comprising: a combination of (i) a silicone acrylate film forming polymer; (ii) a particulate colorant comprising an alumina platelet having a top face and a bottom face and an average thickness of less than 0.5 microns and an average diameter between 1 and 20 microns, having a first colorant comprising a pigment or lake bonded to the top and bottom faces by treatment with triethoxy caprylylsilane; and (iii) a cosmetically acceptable vehicle; wherein the silicone acrylate film forming polymer and the particulate colorant are present in amounts to provide a synergistic enhancement in transfer resistance.

2. The cosmetic composition of claim 1, wherein said treatment with triethoxy caprylylsilane is from about 0.5 wt % to about 2.0 wt % by weight of the particulate colorant.

3. The cosmetic composition of claim 1, wherein the silicone acrylate film forming polymer is selected from the group consisting of butyl acrylate/hydroxypropyldimethicone acrylate copolymer, acrylate/dimethicone copolymer, acrylates/ethylhexyl acrylate/dimethicone methacrylate, and a combination thereof.

4. The cosmetic composition of claim 1, wherein the silicone acrylate film forming polymer comprises butyl acrylate/hydroxypropyldimethicone acrylate copolymer.

5. The cosmetic composition of claim 1, wherein the silicone acrylate film forming polymer comprises acrylate/dimethicone copolymer.

6. The cosmetic composition of claim 1, wherein the silicone acrylate film forming polymer comprises acrylates/ethylhexyl acrylate/dimethicone methacrylate.

7. The cosmetic composition according to claim 1, wherein the composition is in the form of a lipstick or lip gloss.

8. The cosmetic composition according to claim 1, wherein the composition is in the form of a mascara or hair product.

9. The cosmetic composition according to claim 1, wherein the alumina platelet has an edge and the first colorant is adhered to the top and bottom surfaces of the alumina platelet by said treatment with triethoxy caprylylsilane; wherein about 5% to about 90% of the surface area of said platelet is coated with said first colorant and wherein the edge of the platelet is substantially free of said first colorant.

10. The composition of claim 9, wherein the first colorant comprises a pigment.

11. The composition of claim 9, wherein the first colorant comprises a lake.

12. The composition of claim 9, wherein the first colorant has a weight percentage of about 15% to about 60% of the total combined weight percentage of the first colorant and the alumina platelet.

13. The composition of claim 9, wherein the first colorant has a weight percentage of about 15% to about 35% of the total combined weight percentage of the first colorant and the alumina platelet.

14. The composition of claim 9, wherein the first colorant has a weight percentage of about 35% to about 55% of the total combined weight percentage of the first colorant and the alumina platelet.

15. The cosmetic composition of claim 9, wherein said cosmetically acceptable vehicle comprises a silicone fluid having a viscosity of less than 1 cSt at 25° C.

16. A lip stick or lip gloss comprising the cosmetic composition of claim 9.

* * * * *